United States Patent
Aichhorn et al.

(10) Patent No.: US 6,676,603 B2
(45) Date of Patent: Jan. 13, 2004

(54) METHOD AND APPARATUS FOR BEAM COMPOUNDING

(75) Inventors: Manfred Aichhorn, Oberwang (AT); Franz Steinbacher, Vöcklamarkt (AT)

(73) Assignee: Kretztechnik AG, Zipf (AT)

( * ) Notice: Subject to any disclaimer, the term of this patent is extended or adjusted under 35 U.S.C. 154(b) by 34 days.

(21) Appl. No.: 10/047,977

(22) Filed: Nov. 9, 2001

(65) Prior Publication Data

US 2003/0092989 A1 May 15, 2003

(51) Int. Cl.[7] ................................................. A61B 8/00
(52) U.S. Cl. ....................................................... 600/447
(58) Field of Search ................................. 600/437, 440, 600/441–447, 453–458; 73/625, 626; 128/916; 382/128

(56) References Cited

U.S. PATENT DOCUMENTS

| | | |
|---|---|---|
| 4,159,462 A | 6/1979 | Rocha et al. |
| 4,319,489 A | 3/1982 | Yamaguchi et al. |
| 4,649,927 A | 3/1987 | Fehr et al. |
| 6,117,081 A | 9/2000 | Jago et al. |
| 6,224,552 B1 * | 5/2001 | Jago et al. ................ 600/437 |
| 6,283,917 B1 * | 9/2001 | Jago et al. ................ 600/437 |
| 6,373,970 B1 * | 4/2002 | Dong et al. ............... 382/128 |
| 6,416,477 B1 * | 7/2002 | Jago ......................... 600/447 |
| 6,442,289 B1 * | 8/2002 | Olsson et al. ............. 382/128 |
| 6,508,767 B2 * | 1/2003 | Burns et al. .............. 600/443 |
| 6,508,770 B1 * | 1/2003 | Cai ........................... 600/447 |

* cited by examiner

*Primary Examiner*—Ali M. Imam
(74) *Attorney, Agent, or Firm*—McAndrews, Held & Malloy, Ltd.; Peter J. Vogel; Michael A. Dellapenna (57) ABSTRACT

An ultrasound system is disclosed for imaging structure within a subject by generating a compounded image frame having reduced motion artifacts. Ultrasound waves are transmitted into the structure and, for at least one sample volume location within an image plane of the structure, a set of received beams is formed in response to ultrasound waves backscattered from the structure such that the set of received beams intersect at the sample volume location. A compounded data value is generated corresponding to the at least one sample volume location within the image plane based on the corresponding set of received beams. A compounded image frame is formed from at least one compounded data value. Reduced-artifact, compounded imaging at frame rates that are acceptable for abdominal scanning in real-time is also achieved.

30 Claims, 7 Drawing Sheets

METHOD AND APPARATUS FOR BEAM COMPOUNDING

RELATED APPLICATIONS

[Not Applicable]

FEDERALLY SPONSORED RESEARCH OR DEVELOPMENT

[Not Applicable]

BACKGROUND OF THE INVENTION

Certain embodiments of the present invention relate to a medical diagnostic ultrasound system for the purpose of, for example, imaging tissue structure within a human subject. More particularly, certain embodiments relate to a method and apparatus for generating compounded image frames of tissue structure from multiple ultrasound beams along intersecting scan lines in an image plane.

Ultrasound systems have been proposed that employ compounding techniques that combine information sampled from different data frames. For example, the combining technique may include summing or averaging demodulated data from multiple data frames. Several consecutive frames of data are sampled with each frame of data typically being gathered at a unique steering angle. The steering angle is the angle that an ultrasound beam makes in a scan plane with respect to the surface of the ultrasound transducer. The frames of data are then compounded (combined) to create an image frame for display.

Because the data frames are each gathered at a unique steering angle, more information is effectively gathered per sample volume location within a scan plane since reflections from a given sample volume are being viewed at different aspects due to the multiple steering angles. This is analogous to a person viewing a building from significantly different aspects or angles. At each aspect, the person observes different features of the building. There may even be an aspect where the building is blocked and cannot be seen at all. Hopefully, other aspects provide legitimate viewing of the building.

Similarly, for a sample volume of tissue within a scan plane, ultrasound reflections from each aspect will be different, providing different amplitude and phase information back to the ultrasound system. As a result, an image frame with more tissue detail than a frame formed at a single steering angle is provided.

Unfortunately, the resultant compounded image frame may be corrupted due to motion of the tissue during the time delay between successive frames of sampled data. Each frame of data is composed of data gathered from sample volumes of tissue within a scan plane. When motion occurs between one data frame and the next, due to the subject moving with respect to the ultrasound transducer, then data gathered from a given sample volume may appear in a different location in one frame compared to another frame. During compounding of the data frames, data from locations representing different tissue sample volumes will be combined with each other due to the motion. Motion artifacts may result in the compounded image that appear as blurred sample volumes, thus causing detailed tissue information to be lost. The sample volumes in the image lose their sharpness. Hence, the detail of tissue, which could be seen in a compounded image without motion artifact, is lost. Frame-to-frame motion compensation techniques have been employed before compounding to try to reduce motion artifacts. However, the frame-to-frame motion compensation techniques proposed thus far are time consuming, thus degrading frame rate, and sometimes do not compensate well for frame-to-frame motion.

Conventional compounding and scanning techniques are disclosed in the following patents. U.S. Pat. No. 4,649,927 to Fehr et al. is directed to methods and apparatus for producing a compound ultrasound image from overlapping body scans. U.S. Pat. No. 4,319,489 to Yamaguchi et al. is directed to combining images obtained through normal linear scanning and inclined linear scanning. U.S. Pat. No. 6,117,081 to Jago et al. is directed to correcting misregistered images that are to be spatially compounded. U.S. Pat. No. 4,159,462 to Rocha et al. is directed to performing overlapping sector scans.

A need exists for an approach to generating a compounded image frame having enhanced image quality and reduced motion artifacts without having to perform motion compensation. A need also exists to achieve reduced-artifact compounded imaging at frame rates that are acceptable for abdominal scanning in real-time.

BRIEF SUMMARY OF THE INVENTION

An embodiment of the present invention provides an ultrasound system for imaging structure within a subject by generating a compounded image frame having reduced motion artifacts. The system transmits ultrasound waves into the structure and, for at least one sample volume location within an image plane of the structure, forms a set of received beams in response to ultrasound waves backscattered from the structure such that the set of received beams intersect at the sample volume location. A compounded data value is generated corresponding to the at least one sample volume location within the image plane based on the corresponding set of received beams. A compounded image frame is formed from at least one compounded data value.

Apparatus is provided for compounding data values sampled by the ultrasound machine at sample volume locations. The term "compounding" as used throughout means combining multiple data values, either coherently or non-coherently, to create a new, single data value. The apparatus includes a beamformer and transducer array for generation of multiple beams at different steering angles and originating from the same point near the surface of the transducer array. A single data frame is formed by duplicating the formation of the beams such that the beams originate at different points across the lateral dimension of the transducer array. The apparatus further includes a data compounding module to adaptively weight and filter data values from intersecting beams to create a compounded data value corresponding to a sample volume in the scanned image plane. In other words, the compounded image is generated using only the data gathered in a single data frame. One compounded image frame is formed from one data frame. Motion compensation is not required because the intersecting beams for a given sample volume are sampled close enough in time to avoid significant motion artifacts. The apparatus generate a plurality of compounded image frames at a frame rate of at least 4 frames per second for real-time imaging of the structure within the subject.

A method is also provided for compounding data values sampled by an ultrasound machine at sample volume locations within an image plane. The method includes generating a set of multiple beams at different steering angles that originate from the same point at the top of the image plane.

A single data frame is formed by duplicating the method at different points across the lateral dimension of the image plane. The method further includes data compounding to adaptively weight and filter data values from intersecting beams to create a compounded data value corresponding to a sample volume in the scanned image plane. In other words, the compounded image is generated using only the data gathered in a single data frame. One compounded image frame is formed from one data frame. Motion compensation is not required because the intersecting beams for a given sample volume are sampled close enough in time to avoid significant motion artifact.

Certain embodiments of the present invention afford an approach to generating a compounded image frame having reduced motion artifact without having to perform motion compensation. Reduced-artifact compounded imaging at frame rates that are acceptable for abdominal scanning in real-time is also achieved.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION OF THE INVENTION

Figure 1:
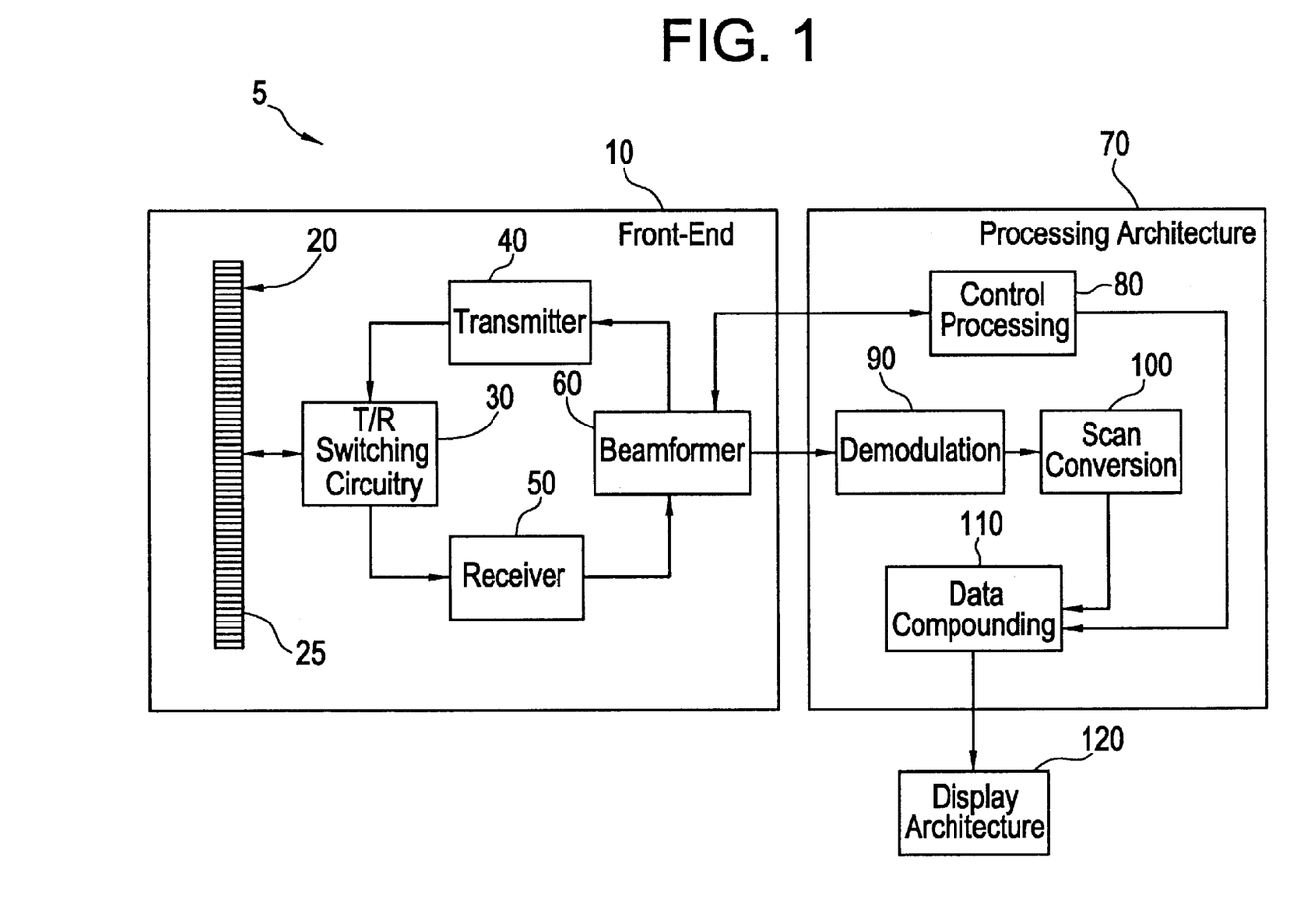
FIG. 1 is a schematic block diagram of an ultrasound system formed in accordance with an embodiment of the present invention.

FIG. 1 is a schematic block diagram of an ultrasound system 5 showing the major elements used for beam compounding in accordance with an embodiment of the present invention. The illustrated elements of the ultrasound system 5 are the front-end 10, the processing architecture 70, and the display architecture 120. Front-end 10 comprises a transducer array 20 (comprising a plurality of transducer array elements 25), transmit/receive switching circuitry 30, a transmitter 40, a receiver 50, and a beamformer 60. Processing architecture 70 comprises a control processing module 80, a demodulation module 90, a scan conversion module 100, and a data compounding module 110.

The architectures and modules may be dedicated hardware elements such as circuit boards with digital signal processors or may be software running on a general purpose computer or processor such as a commercial, off-the-shelf PC. The various architectures and modules may be combined or separated according to various embodiments of the present invention.

In the front-end 10, the transducer array 20 is connected to the transmit/receive (T/R) switching circuitry 30. The T/R switching circuitry 30 is connected to the output of transmitter 40 and the input of receiver 50. The output of receiver 50 is input to beamformer 60. Beamformer 60 is further connected to the input of transmitter 40, to control processing module 80 and the input of demodulation module 90 in processing architecture 70.

Figure 2:
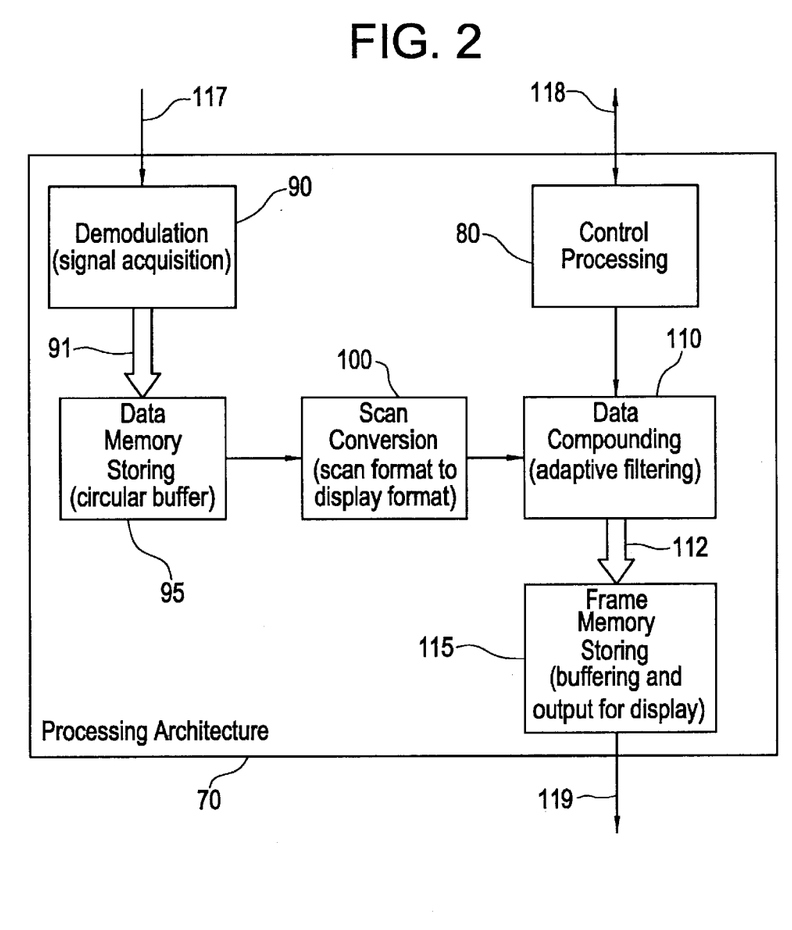
FIG. 2 is a more detailed schematic block diagram of the processing architecture in FIG. 1.

FIG. 2 illustrates a more detailed schematic block diagram of the processing architecture 70 of FIG. 1. This detailed embodiment comprises a control processing module 80, a demodulation module 90, a direct memory access (DMA) interface 91, a data memory module 95, a scan conversion module 100, a data compounding module 110, a direct memory access (DMA) interface 112, and a frame memory module 115.

In processing architecture 70, the DMA interface 91 is connected between the output of demodulation module 90 and the input of data memory module 95. The output of data memory module 95 is connected to the input of scan conversion module 100. The output of scan conversion module 100 is connected to an input of data compounding module 110. Control processing module 80 is connected to data compounding module 110. DMA interface 112 is connected between the output of data compounding module 110 and the input of frame memory module 115. The output of frame memory module 115 is connected to the input of display architecture 120.

When a frame of data is to be sampled from a subject, the transducer array 20 is used to transmit ultrasound waves into the subject. The transducer array 20 may be a linear array or curved array of many individual transducer elements 25. Each transducer element 25 is capable of generating ultrasound waves in response to a signal from the transmitter 40. In addition, the phase relationship of the ultrasound waves between transducer elements 25 can be controlled. The result is an ultrasound beam (e.g. 151 in FIG. 3) of energy being transmitted into the tissue of a subject at a certain angle (e.g. 144) with respect to an orthogonal direction 149 to the surface 143 of the transducer array 20 and effectively originating from a point (e.g. 132) on the surface 143 of the transducer array 20. Multiple elements 25 are typically used to transmit an ultrasound beam (e.g. 151). The phase relationship between the ultrasound waves transmitted from the multiple elements 25 determines the steering angle (e.g. 144) of the beam (e.g. 151) being transmitted. The number of transducer elements 25 used for transmission, as well as other factors such as apodization, determine the shape of an ultrasound beam (e.g. 151) along its length within the tissue structure.

When scanning with a transducer array 20, data is collected from a scan plane 121 (see FIG. 3) within a subject to create a data frame 170 (see FIG. 6) within the ultrasound system 5. The data frame 170 is made up of received ultrasound beams 171 of data that follow along different scan lines (e.g. 122–131) within the scan plane 121. Ultrasound beams 171 are transmitted and received at different times along different scan lines (e.g. 122–131 in FIG. 3) in the scan plane 121 according to a predetermined sequence. The beams 171 originate at different points (e.g. 132–142 in FIG. 3) along the surface 143 of the transducer array 20 and form different steering angles (e.g. 144–148 in FIG. 3), within the scan plane 121, with respect to an orthogonal direction 149 to the surface 143 of the transducer array 20.

Figure 3:
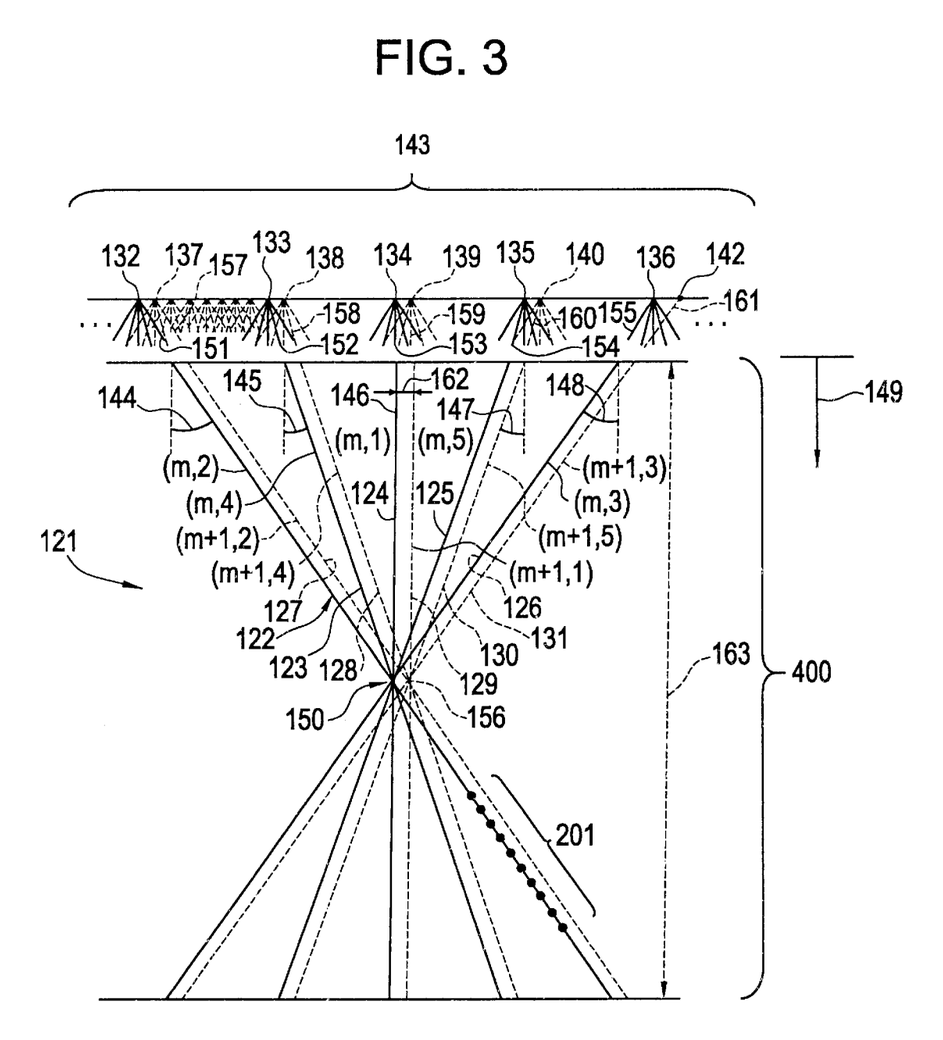
FIG. 3 illustrates a scanning technique used in accordance with an embodiment of the present invention.

FIG. 3 illustrates several scan lines 122–131 along which ultrasound beams 171 are transmitted at various steering angles 144–148 within a scan plane 121. All of the beams originate from points on the surface 143 of the transducer array 20. For example, to sample data from a particular sample volume location 150 within a scan plane 121 at five different steering angles 144–148, five separate beams 151–155 are transmitted and received originating from points 132–136 along scan lines 122–126. The sequence of five beams 151–155 intersect at sample volume location 150. The five scan lines 122–126 along which the sequence of five beams 151–155 are transmitted and received are identified according to a sequence number m and a beam number n within the sequence m as (m,n). The five scan lines 122–126 are represented in FIG. 3 as (m,1) to (m,5). For an adjacent sample volume location 156, another sequence of five beams 157–161 represented as (m+1,1) to (m+1,5) intersect at sample volume location 156 within the scan plane 121. Each of the five beams 157–161 along scan lines 127–131 corresponding to sequence m+1 originate at points 137–142 on the surface 143 of the transducer array 20 and are offset from the corresponding points 132–136 for the sequence m by a distance $d_s$ 162.

Any complete sequence, m, of received beams (e.g. 151–155) contributes only to one sample volume location (e.g. 150) within a scan plane 121. All the received beams 171 are shared between sample volume locations, however. To generate data for a complete data frame 170, many ultrasound beams 171 must be transmitted and received along many scan lines (e.g. 122–131) such that, in this example, there are five intersecting beams (e.g. 151–155) for every sample volume location (e.g. 150) within the scan plane 121.

For example, if an image frame 190 (see FIG. 6) is to be made up of 200 resultant vertical, compounded lines of data 186 across the scan plane 121 and each of the received beams 171 contributes data for each depth (e.g. 163) over a total depth 400 of a scan plane 121, then an uncompounded data frame 170 will be made up of 5*200=1000 intersecting received beams 171 of data (assuming that each sample volume location requires a sequence of five intersecting beams).

To generate a transmitted ultrasound beam (e.g. 151) along a scan line (e.g. 122), the control processing module 80 sends command data to the beamformer 60 which tells the beamformer to generate transmit parameters to create a beam (e.g. 151) of a certain shape that originates from a certain point (e.g. 132) at the surface 143 of the transducer array 20 at a certain steering angle (e.g. 144). The transmit parameters are sent from the beamformer 60 to the transmitter 40. The transmitter 40 uses the transmit parameters to properly encode transmit signals to be sent to the transducer array 20 through the T/R switching circuitry 30. The transmit signals are set at certain levels and phases with respect to each other and are provided to individual transducer elements 25 of the transducer array 20. The transmit signals excite the transducer elements 25 of the transducer array 20 to emit ultrasound waves with the same phase and level relationships. In this way, a transmitted beam (e.g. 151) of ultrasound energy will be formed in the tissue structure of the subject within a scan plane 121 when the transducer array 20 is acoustically coupled to the subject by using, for example, ultrasound gel. This process is known as electronic scanning.

The transducer array 20 is a two-way transducer. Once ultrasound waves are transmitted into a subject, the ultrasound waves are backscattered off of tissue sample volumes (e.g. 150) within the structure. The backscattered waves arrive at the transducer array 20 at different times, depending on the distance into the tissue they returned from and the angle with respect to the surface 143 of the transducer array 20 at which they return. The transducer elements 25 of the transducer array 20 are responsive to these backscattered waves and convert the ultrasound energy from these backscattered waves into received electrical signals.

The received electrical signals are routed through the T/R switching circuitry 30 to the receiver 50. The receiver 50 amplifies and digitizes the received signals and provides other functions such as gain compensation. The digitized received signals correspond to the backscattered waves received by each transducer element 25 at various times and preserve the amplitude and phase information of the backscattered waves.

The digitized received signals are sent to beamformer 60. The control processing module 80 sends command data to beamformer 60. Beamformer 60 uses this command data to form a receive beam (e.g. 151) originating from a point (e.g. 132) on the surface 143 of transducer array 20 at a steering angle (e.g. 144) typically corresponding to the point and steering angle of the previous ultrasound beam (e.g. 151) transmitted along a scan line (e.g. 122). The beamformer 60 operates on the appropriate received signals by performing time delaying and focusing, according to the instructions of the command data from the control processing module 80, to create received beam (e.g. 151) signals corresponding to sample volumes (e.g. the subset 201) along a scan line (e.g. 122) in the tissue structure of the subject. The phase, amplitude, and timing information of the received signals from the various transducer elements 25 is used to create the received beam (e.g. 151) signals.

Figure 4:
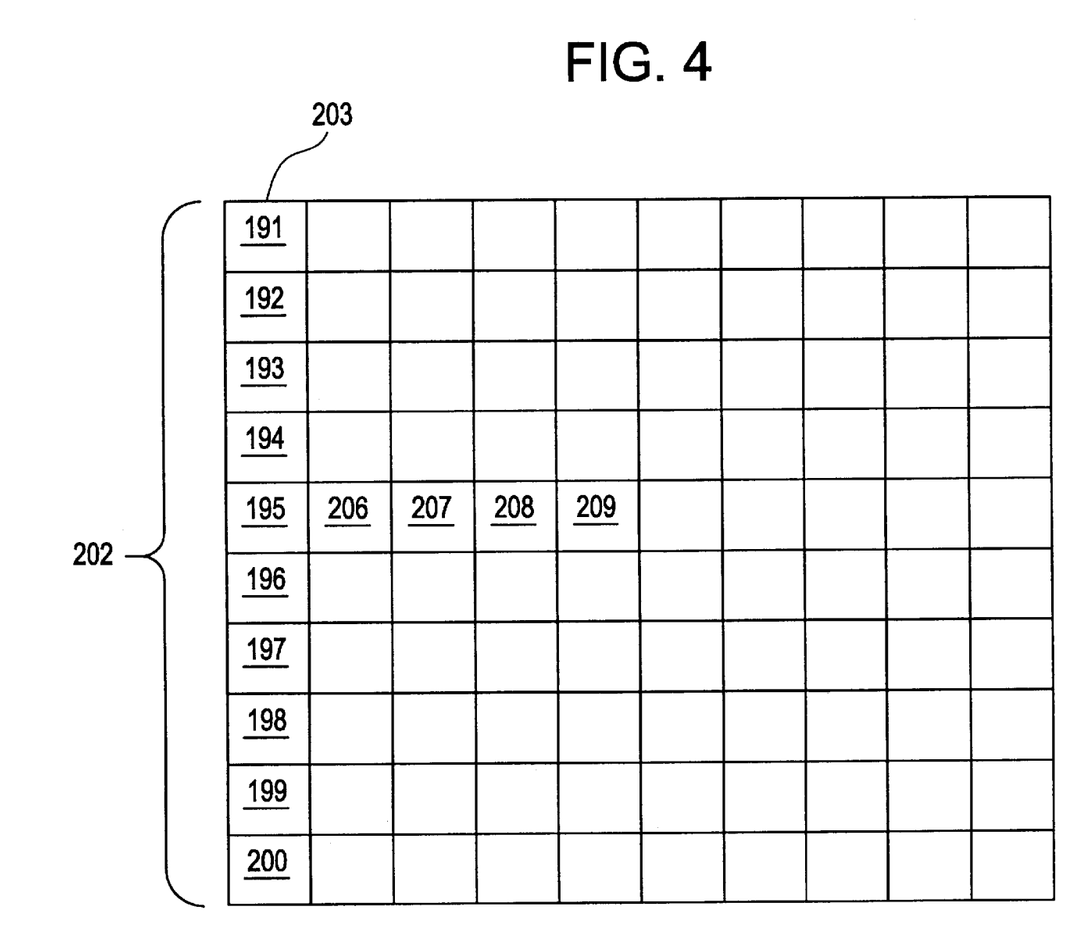
FIG. 4 illustrates how data may be stored in data memory in the order that it is received for each beam of data.

The received beam (e.g. 151) signals are sent to processing architecture 70 over digital interface 117. Demodulation module 90 performs demodulation on the received beam (e.g. 151) signals to create pairs of I and Q demodulated data values (e.g. the subset 191–200 in FIG. 4) corresponding to sample volumes (e.g. the subset 201 in FIG. 3) along the length of a scan line (e.g. 122) corresponding to the received beam (e.g. 151). The I and Q demodulated data values preserve the phase and amplitude information of the received signals. Extracting the amplitude information from an I and Q data pair for a given sample volume location (e.g. 150) is mathematically equivalent to performing the operation $\sqrt{I^2+Q^2}$. Thus, a single amplitude data value is yielded (e.g. 191 in FIG. 4). The phase information is lost once amplitude detection is performed on the data and the original I and Q data is discarded. Amplitude detection is performed by the demodulation module 90 as part of the demodulation function. Subsequent processing such as scan conversion and compounding is non-coherent because the phase information is not used.

Optionally, the I and Q demodulation data can be preserved (no amplitude detection performed by the demodulation module 90) and used for subsequent processing such as scan conversion and compounding. This would correspond to coherent compounding of the data.

The demodulated data (e.g. the subset 191–200) is transferred to data memory module 95 over DMA interface 91. The DMA interface 91 controls the transfer of data between demodulation module 90 and data memory module 95. The DMA interface 91 has the starting address of the data memory location where the demodulation data (e.g. the subset 191–200) for a particular received beam (e.g. 151) is to be written. There is no required handshaking required between the demodulation module 90 and data memory module 95. Therefore, when demodulation data (e.g. the subset 191–200) is available from the demodulation module 90, the DMA interface 91 is able to quickly transfer the demodulation data (e.g. the subset 191–200) to data memory module 95 without any delays caused by handshaking.

The demodulation data (e.g. the subset 191–200) in data memory module 95 is stored in scan sequence format (i.e. the order in which the samples were collected). For example, referring to FIG. 4, the subset of demodulation data 191–200 for N sample volume locations 201 (see FIG. 3) along the length of a particular received beam (e.g. 151), corresponding to a particular beam sequence m and a beam number n (e.g. (m,2)), may be stored in N successive memory locations 202 in a portion of data memory module 95.

Column 203 in data memory module 95 corresponds to a beam number n of a beam sequence m (e.g. (m,2)). However, the received beam (e.g. 151) may correspond to a scan line (e.g. 122) that originates at a point (e.g. 132) one fourth of the way from one end of the transducer array 20 and cuts at a steering angle (e.g. 144) across the scan plane 121. In order for the demodulation data 191–200 to end up contributing to the correct locations in an image plane 190 (FIG. 6) upon display, the data 191–200 must be converted or translated to image coordinate format.

Figure 5:
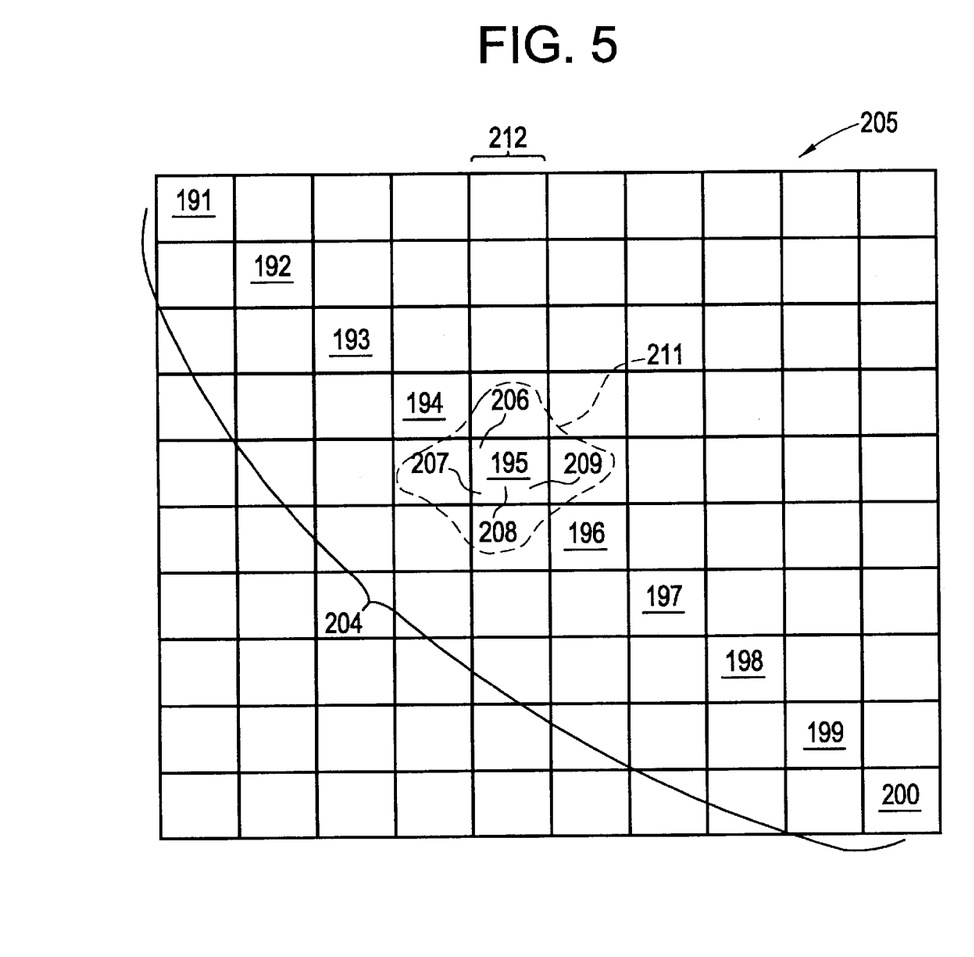
FIG. 5 illustrates how data stored in data memory is translated during scan conversion to locations in an image plane representation.

The translation is performed by scan conversion module 100 and is illustrated in FIG. 5. The data 191–200 corresponding to the N sample volume locations 201 has been scan converted to correspond to the proper N locations 204 within an image plane 205. The final compounded frame of data that gets processed and displayed by display architecture 120 is a 2-dimensional image frame 190 in rectangular coordinates (the image coordinate format). The scan conversion module 100 is programmed to take the demodulation data (e.g. 191–200), which is in a particular scan sequence format, and convert it to a rectangular coordinate system. For each particular receive beam (e.g. 151), the scan conversion module knows the orientation of the beam. The scan conversion module is implemented so as to interpolate data between neighboring sample volumes (e.g. 150 and 156) in the image plane 205 to generate the scan converted data samples (e.g. the subset 191–200 in FIG. 5) in image coordinate format.

The scan converted data (e.g. the subset 191–200 and the subset 206–209 in FIG. 5) is sent to the data compounding module 110. The data compounding module 110 combines multiple scan converted data values (e.g. 195, 206, 207, 208, and 209 in FIG. 4) corresponding to a single sample volume location (e.g. 150) or image point (e.g. 210 in FIG. 6) in an image plane 205 into a single compounded data value 211 (FIG. 5 and FIG. 6 where compounded data value 211 is a function of, for example, data values 195, 206, 207, 208, and 209). An adaptive filtering technique is employed to perform the data compounding function. This is discussed in more detail below.

As scan converted data (e.g. the subset 195, 206, 207, 208, and 209) is compounded by the data compounding module 110, the DMA interface 112 stores the compounded data in frame memory module 115. The DMA interface 112 controls the transfer of data between data compounding module 110 and frame memory module 115. The DMA interface 112 has the starting address of the frame memory location where the compounded data for a particular vertical image line (e.g. 212 in FIG. 5 and FIG. 6) is to be stored. There is no handshaking required between the data compounding module 110 and frame memory module 115. Therefore, when compounded data is available from the data compounding module 110, the DMA interface 112 is able to quickly transfer the compounded data to frame memory module 115 without any delays caused by handshaking.

Optionally, the frame memory module 115 may include two buffers of memory. While one buffer is being written to by the DMA interface 112, the other buffer is being read out by display architecture 120 so that the frame can be displayed to an operator. Once the second buffer has been read out for display, it is then written to again by DMA interface 112 with the next incoming frame of compounded data while the previous first buffer written to is read out for display. The operation of the frame memory buffers alternates back and forth between being written to and being read out. Hence, the two memory buffers maintain adequate frame rates.

The display architecture 120 comprises various elements to provide the functions of performing any final spatial or temporal filtering, applying grayscale or color to the compounded data, and converting the digital data to analog data for display by, for example, a cathode ray tube monitor.

To form a single compounded data value (e.g. 211) for a sample volume location (e.g. 150) with very little motion artifact, a sequence of intersecting received beams (e.g. 151–155) is formed within a predetermined time interval for the sample volume location (e.g. 150) within the scan plane 121 to be imaged, as previously described.

Referring to FIG. 3, a particular sample volume location 150 is shown as the point of intersecting scan lines 122–126. Here, a sequence of five received beams (m,1) to (m,5) 151–155 are formed such that they intersect at a single sample volume location 150 in the scan plane 121. Each received beam 151–155 originates at a different point 132–136 along the face 143 of the transducer array 20 and is at a different steering angle 144–148. In this way, the sample volume location 150 (point of intersection) is effectively viewed by the transducer array 20 from five different angles 144–148. Five times as much information is gathered for the sample volume location 150 as would typically be gathered for a sample volume location in a single frame of data.

For a particular sample volume location 150, the five corresponding data samples (e.g. 195, 206–209 in FIG. 4), one from each intersecting beam 151–155, are demodulated by demodulation module 90 and scan converted by scan conversion module 100 as previously described. The five resultant scan converted samples (e.g. 195, 206–209 in FIG. 5) are then compounded in the data compounding module 110. The data compounding module 110 combines the five scan converted samples (e.g. 195, 206–209 in FIG. 5) by adaptively weighting and filtering the samples according to the following expression:

$$g = \sum_{i=1}^{N} \left\{ [g_i * p_i(g_i)] \prod_{k=1}^{i-1} [1 - p_k(g_k)] \right\} \quad \text{[Equation 1]}$$

where g is the resulting compounded data value for the sample volume location (e.g. 150), $g_i$ is the scan converted data value for the $i^{th}$ received beam for the sample volume location (e.g. 150), $p_i(g_i)$ and $p_k(g_k)$ are weighting coefficients with values between [0,1] which are a function of $g_i$ and $g_k$ respectively and the steering angle of received beam i and k respectively, and N is the number of different beams and steering angles which is 5 in the example of FIG. 3.

Equation 1 allows a resultant compounded data value g to be weighted according to the demodulation values (e.g. 195 and 206–209) and corresponding steering angles (e.g. 144–148) of the different samples for a given sample volume location (e.g. 150). Enhanced flexibility is, therefore, provided in achieving a desired image quality (e.g. contrast resolution) based on the application and is what makes the compounding adaptive. The weighting coefficients can be downloaded from control processing module 80 to data compounding module 110 depending on the application selected by the user. Other criteria can be used, as well, to determine which set of coefficients to use.

Figure 6:
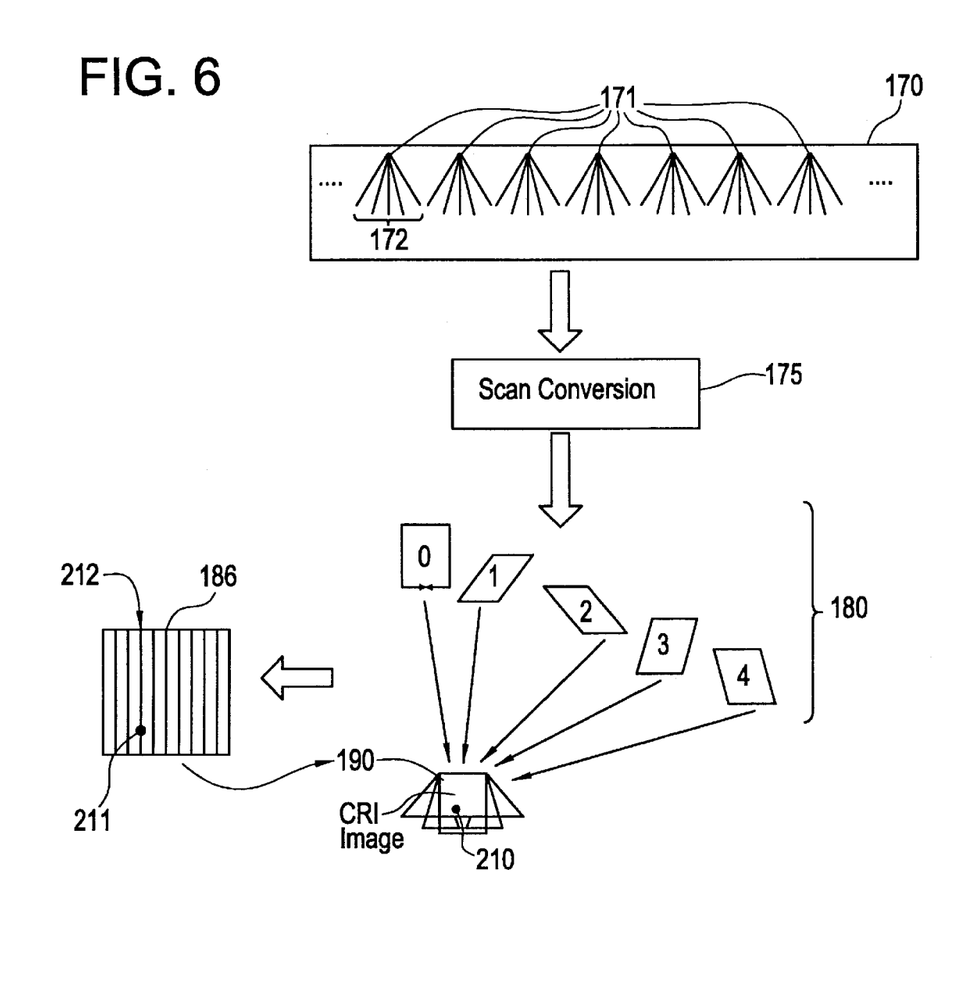
FIG. 6 illustrates a graphical representation of how beam data is stored, scan converted and compounded in accordance with an embodiment of the present invention.
Figure 7:
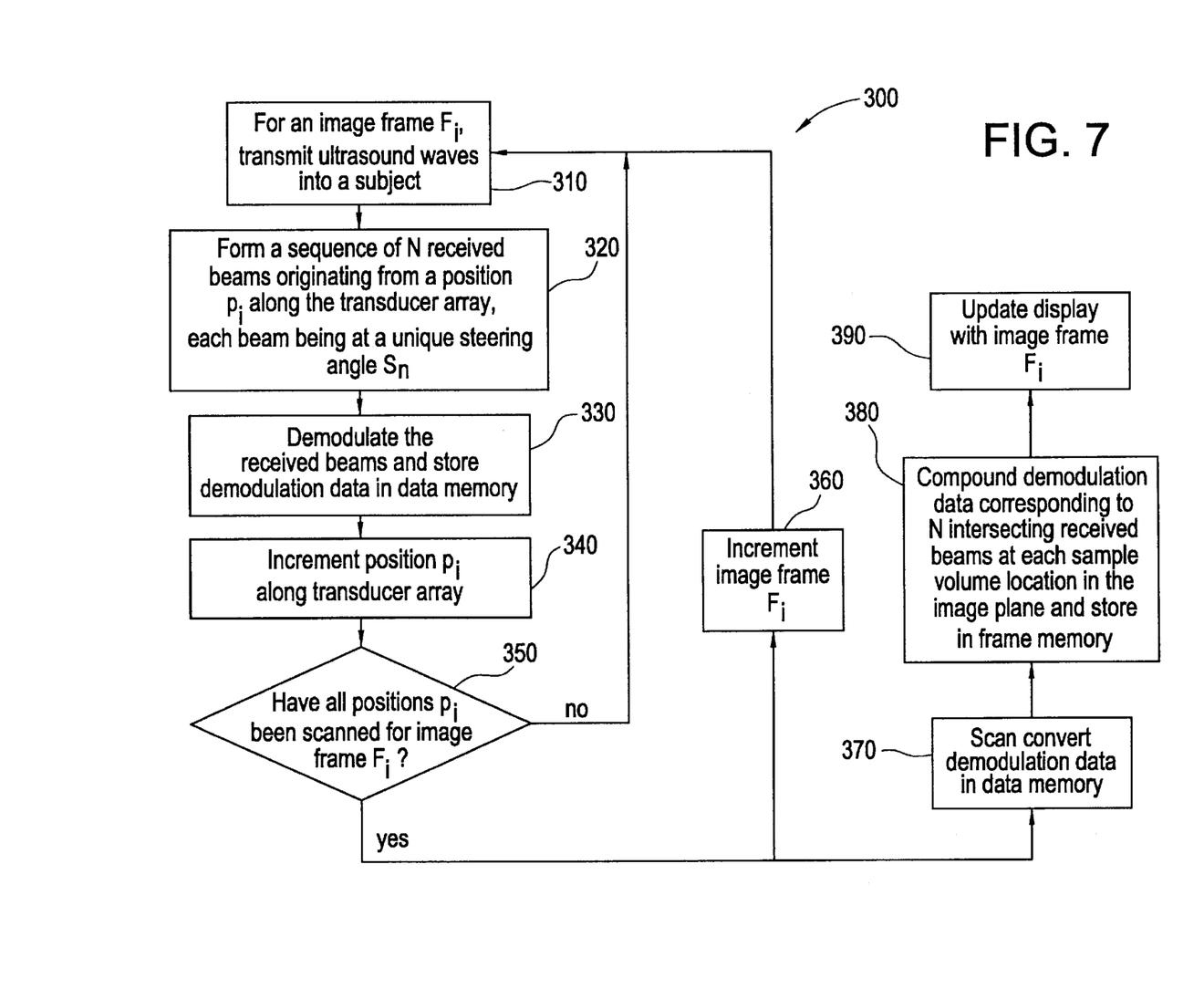
FIG. 7 is a flowchart illustrating a method employed to form successive compounded image frames in accordance with an embodiment of the present invention.

Next, FIGS. 6 and 7 are discussed in connection with a method to form a single compounded image frame $F_j$ 190 from a single data frame 170 with limited motion artifact. A sequence of N intersecting received beams (e.g. 151–155) is formed for each sample volume location (e.g. 150) within a scan plane 121 to be imaged.

FIG. 7 illustrates a beam compounding method 300 of creating a single compounded image frame $F_j$ 190 and subsequent compounded image frames $F_{i+1}, F_{j+2}, \ldots, F_{j+m}$. In step 310 of the method, ultrasound waves are transmitted into a subject along scan lines such that, in step 320, a set of N received beams (172) is formed originating from a position $p_i$ (e.g. 132 in FIG. 3) on the surface 143 of the transducer array 20. Each received beam in the set 172 is at a unique, pre-defined steering angle $S_n$ (e.g. 144–148).

In step 330, the set of received beams 172 are demodulated by demodulation module 90 and the resultant data values (e.g. the subset 191–200) are stored in data memory module 95. In step 340, i is incremented so scanning can be performed with respect to the next position $p_{i+1}$ (e.g. 137 in FIG. 3) along the face 143 of the transducer array 20. The beam compounding method 300 checks, in step 350, to determine if all the positions $p_i$ along the face 143 of the transducer array 20 have been scanned for image frame $F_j$ 190. If not, then processing reverts to step 310 to transmit and collect data for the next point along the face of the transducer array $p_{i+1}$. Steps 310–350 are repeated until all of the required beam sequences m have been transmitted and received to collect enough data to form a single image frame $F_j$ 190.

FIG. 6 graphically illustrates the operations carried out during the method of FIG. 7. Reference number 170 denotes that all of the raw demodulation data for the received beams is stored in data memory module 95. As described previously, if 200 resultant compounded vertical image lines of data 186 are required to form image frame $F_j$ 190 and N=5 intersecting received beams (e.g. 151–155) are required for each sample volume location (e.g. 150), then 1000 received beams 171 at the various steering angles (e.g. 144–148) should be generated to form the compounded image frame 190.

Once all the positions $p_i$ along the face 143 of the transducer array 20 have been scanned, the method of FIG. 7 proceeds to step 370 where the demodulation data (e.g. the subset 191–200) for the image frame $F_j$ 190 stored in data memory module 95 is scan converted as previously described (see FIG. 5 and FIG. 6). Since scan conversion is being done before compounding, a large amount of data is scan converted, namely N times more data than would be scan converted for an image formed from a single series of scan lines. The image frame $F_j$ is also incremented to $F_{j+1}$ in step 360 and the method reverts to step 310 to begin transmitting and collecting data for the next image frame.

The data scan converted at step 370 (e.g. the subset 195, 206–209) is sent to data compounding module 110 and is compounded in step 380 for each sample volume location (e.g. 150) corresponding to the intersection of N received beams (e.g. 151–155) based on Equation 1 as described previously. Weighting coefficients (as defined for Equation 1) are downloaded from control processing module 80 to data compounding module 110 based on the application selected by the operator. FIG. 6 graphically illustrates that all of the data 180 collected from the N different steering angles (e.g. 144–148) is compounded. The compounded data values (e.g. 211) are stored in frame memory module 115 and output for display to display architecture 120 in step 390. In this way, real-time imaging of a scan plane 121 in a subject is achieved. With the method of FIG. 7, frame rates of 9 to 12 Hz may be achieved for abdominal applications.

As an example, for a desired compounded image frame $F_j$ 190 that includes 200 vertical lines of compounded data 186 corresponding to 200 sample origin points $p_i$ (e.g. a subset would be 132–142) along the face 143 of the transducer array 20, N=5 received beams (e.g. 172) are formed for each point $p_i$ (e.g. 132). This yields 200*5=1000 received beams of data 170 that must be formed to generate a single compounded image frame 190. The N beams (e.g. 151–155) that intersect at a given sample volume location (e.g. 150) are formed in a short enough period of time with respect to each other to render any motion artifact at the sample volume location (e.g. 150) insignificant. The operator will see a significant image quality enhancement (e.g. improved contrast resolution) in the compounded image 190 over a similar image where compounding has not been performed. No motion compensation steps are necessary because the effect of motion has inherently been taken out in the sampling of method 300. The compounded image frame 190 is formed from the data collected for a single data frame 170.

To further illustrate this example, if the frame rate is 10 Hz, then the time to generate a single frame of compounded data is 0.1 seconds. The time to generate any one of the 1000 received beams to form the image is, on average, 100 micro-seconds. Assuming the speed of sound in tissue is about 1 centimeter per 13 micro-seconds, then this corresponds to imaging to a depth 400 of about 7.7 centimeters. The minimum amount of time to create 5 intersecting beams for a single sample volume location is then about 500 micro-seconds. A time interval of 500 micro-seconds will contribute negligibly to any motion artifacts for the sample volume location.

The maximum amount of time to create 5 intersecting beams for a single sample volume location would be the time interval between frames or 0.1 seconds for the 10 Hz frame rate, and could introduce more significant motion artifact that would degrade the image quality. When the data 170 is collected in serial order across the face 143 of the transducer array 20, for a frame rate of 10 Hz and imaging down to a depth 400 of about 7.7 cm, the typical time to create 5 intersecting beams (e.g. 151–155) for a single sample volume location (e.g. 150) is on the order of 30 milli-seconds and results in a significant enhancement in image quality (e.g. improved contrast resolution) over that achieved by not compounding.

Optionally, beam compounding may be performed before scan conversion. The amount of data that would have to be scan converted for the formation of a single compounded image frame would be minimized. However, the improvement in image quality may not be as great since sample volume locations may not be properly aligned before compounding as they are by scan conversion before compounding. Also, other methods or variations of compounding the data can be performed instead of strictly using Equation 1.

Optionally, data from the data memory module could begin to be processed by the scan conversion module and data compounding module before all of the data for a single frame has been collected in the data memory module. A pipe-lined method of data transfer that could enhance frame rates would be provided. Also, the generation of successive sequences of N beams would not have to be done in serial order across the face of the transducer array. It may prove to be more effective and efficient to skip over certain positions on the face of the transducer array to generate sequences of beams out of order and then come back to the skipped positions. A further reduction in motion artifacts and enhanced frame rates may be achieved.

In summary, the advantages and features include, among others, enhanced image quality without significant motion artifacts. There is no need to perform motion compensation to achieve these results. The motion compensation is inherent in the sampling and compounding method.

While the invention is described in connection with one embodiment, it will be understood that the invention is not limited to that one embodiment. On the contrary, the invention covers all alternatives, modifications, and equivalents within the spirit and scope of the appended claims.

What is claimed is:

1. In an ultrasound system for imaging structure within a subject, an apparatus for generating a compounded image frame having reduced motion artifacts, said apparatus comprising:
    a front-end for transmitting temporally distributed ultrasound waves into the structure and, for at least one sample volume location within an image plane of the structure, forming over time a set of received beams temporally separated in response to ultrasound waves backscattered from the structure, said set of received beams intersecting at said sample volume location; and
    a processing module receiving said set of received beams and generating a compounded data value corresponding to said at least one sample volume location within said image plane based on said set of received beams, said processing module forming a compounded image frame from at least one said compounded data value,
    wherein said set of received beams intersecting at said sample volume location are formed in less than a single frame time.

2. The apparatus of claim 1 wherein said set of received beams comprises at least three intersecting received beams arranged in a common image plane and obtained from a sequence of transmitted ultrasound waves.

3. The apparatus of claim 1 wherein said processing module generates a set of demodulated data values from said set of received beams corresponding to said at least one sample volume location.

4. The apparatus of claim 1 wherein said processing module generates a set of scan converted data values from said set of received beams corresponding to said at least one sample volume location.

5. The apparatus of claim 1 wherein said processing module generates a scan converted data value from said at least one compounded data value corresponding to said at least one sample volume location.

6. The apparatus of claim 1 wherein said processing module adaptively filters a set of scan converted signals, in part, by weighting elements of said set of scan converted signals as a function of amplitude and steering angle, to generate said compounded data value corresponding to said at least one sample volume location.

7. The apparatus of claim 1 wherein said processing module adaptively filters a set of demodulation signals, in part, by weighting elements of said set of demodulation signals as a function of amplitude and steering angle, to generate said compounded data value corresponding to said at least one sample volume location.

8. The apparatus of claim 1 wherein said first and second received beams originate at first and second locations on a transducer at different instances in time, said forming over time including said first and second received beams in said set of received beams.

9. The apparatus of claim 1 wherein said forming over time includes, in said set of received beams, first and second received beams formed in response to first and second ultrasound waves backscattered at different times.

10. The apparatus of claim 1 wherein, during separate first and second scans, first and second received beams are originated at first and second steering angles, respectively, with respect to a transducer.

11. In an ultrasound system for imaging structure within a subject, a method for generating a compounded image frame having reduced motion artifacts, said method comprising:
    transmitting ultrasound waves into the structure during a series of scans;
    forming a set of received beams over said series of scans for at least one sample volume location within an image plane of the structure in response to ultrasound waves backscattered from the structure, said set of received beams intersecting at said sample volume location;
    generating a compounded data value corresponding to said sample volume location within said image plane based on said set of received beams; and
    forming a compounded image frame from at least one said compounded data value,
    wherein said set of received beams intersecting at said sample volume location are formed in less than a single frame time.

12. The method of claim 11 further comprising the step of generating a plurality of compounded image frames at a frame rate of at least four frames per second for real-time imaging of the structure within the subject.

13. The method of claim 11 wherein said set of received beams comprises at least three intersecting received beams arranged in a common image plane.

14. The method of claim 11 further comprising the step of generating a set of demodulated data values from said set of received beams corresponding to said at least one sample volume location.

15. The method of claim 11 further comprising the step of generating a set of scan converted data values from said set of received beams corresponding to said at least one sample volume location.

16. The method of claim 11 further comprising the step of generating a scan converted data value from said at least one said compounded data value corresponding to said at least one sample volume location.

17. The method of claim 11 further comprising the step of adaptively filtering data values associated with said set of received beams based on weighting elements of said data values as a function of amplitude and steering angle, to generate said compounded data value corresponding to said at least one sample volume location.

18. The method of claim 11 further comprising originating first and second received beams at first and second locations on a transducer at different instances in time, said forming step including said first and second received beams in said set of received beams.

19. The method of claim 11 wherein said forming step includes, in said set of received beams, first and second received beams formed in response to first and second ultrasound waves backscattered at different times.

20. The method of claim 11 further comprising originating, during separate first and second scans, first and second receive beams at first and second steering angles, respectively, with respect to a transducer.

21. A medical diagnostic ultrasound system comprising:
a transducer transmitting ultrasound signals and receiving ultrasonic echoes;
a beamformer deriving data samples representative of said ultrasonic echoes along at least two scan lines in an image plane, said scan lines intersecting one another at a sample point in said image plane;
a data compounding module producing a composite data value from said data samples derived by said beamformer along said at least two scan lines; and
a display subsystem producing a compounded image frame corresponding to said image plane based on at least one said composite data value
wherein said ultrasonic echoes along said at least two scan lines are formed in less than a single frame time.

22. The ultrasound system of claim 21 wherein a plurality of compounded image frames is generated at a frame rate of at least four frames per second for real-time imaging of a structure within a subject.

23. The ultrasound system of claim 21 further comprising a scan conversion module to generate scan converted data values.

24. The ultrasound system of claim 21 wherein said data samples are demodulated data values corresponding to said sample point in said image plane.

25. The ultrasound system of claim 21 wherein said data samples are scan converted data values corresponding to said sample point in said image plane.

26. The ultrasound system of claim 21 wherein said composite data value is a scan converted data value corresponding to said sample point in said image plane.

27. The ultrasound system of claim 21 wherein said data compounding module adaptively filters said data samples, in part, by weighting said data samples as a function of amplitude and steering angle, to produce said composite data value corresponding to said sample point in said image plane.

28. The ultrasound system of claim 21 wherein first and second received beam signals originate at first and second locations on said transducer at different instances in time, said data samples including said first and second received beam signals in said ultrasonic echoes.

29. The ultrasound system of claim 21 wherein said data samples includes first and second received beam signals formed in response to first and second ultrasonic echoes backscattered at different times.

30. The ultrasound system of claim 21 wherein, during separate first and second scans, first and second received beams are originated at first and second steering angles, respectively, with respect to said transducer.

* * * * *